United States Patent
Maienfisch et al.

[11] Patent Number: 5,481,013
[45] Date of Patent: Jan. 2, 1996

[54] CARBOXYLIC ACID DERIVATIVES

[75] Inventors: Peter Maienfisch, Rodersdorf; Thomas Pitterna, Basel, both of Switzerland; Manfred Böger, Weil am Rhein, Germany

[73] Assignee: Ciba-Geigy Corporation, Tarrytown, N.Y.

[21] Appl. No.: 81,598

[22] Filed: Jun. 23, 1993

[30] Foreign Application Priority Data

Jun. 30, 1992 [CH] Switzerland ............................ 2038/92

[51] Int. Cl.⁶ .................................................. C07C 69/62
[52] U.S. Cl. .................... 554/226; 554/225; 546/298; 548/127; 548/128; 548/129; 558/266; 558/271; 558/257; 558/234; 560/32; 560/65; 560/219; 560/227; 564/207
[58] Field of Search .................... 554/226, 225; 546/298; 548/127, 128, 129; 558/266, 271, 234, 257; 560/32, 65, 219, 227; 564/207; 514/533, 548, 549

[56] References Cited

U.S. PATENT DOCUMENTS

| 4,950,666 | 8/1990 | Peake et al. ...................... 514/277.5 |
| 5,081,287 | 1/1992 | Peake et al. ...................... 560/219 |

FOREIGN PATENT DOCUMENTS 432861  6/1991  European Pat. Off. .

*Primary Examiner*—Paul J. Killos
*Attorney, Agent, or Firm*—Kevin Mansfield; Marla J. Mathias

[57] ABSTRACT

Compounds of the formula

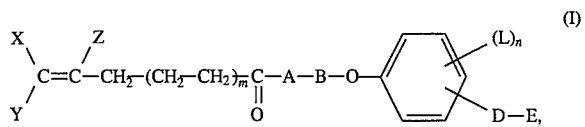

in which
A is oxygen, sulfur or —NR₁—;
B is C₂–C₆alkylene,
D-E is —O—E, —S—E, —O—CH₂—E, —O—C(=O)—E, —O—C(=O)—O—E, —O—C(=O)—N(H)—E or —O—C(=S)—N(H)—E;
E is phenyl; phenyl which is substituted by one to three substituents; a five-membered aromatic heterocycle having one to three hetero atoms; a five-membered aromatic heterocycle which has one to three hetero atoms and which is substituted by one or two substituents; a six-membered aromatic heterocycle which has one to three nitrogen atoms; or a six-membered aromatic heterocycle which has one to three nitrogen atoms and which is substituted by one or two substituents;
L is halogen or methyl;
X is fluorine;
Y is chlorine or fluorine;
Z is hydrogen, fluorine or methyl;
m is the number zero, one, two, three, four or five;
n is the number zero, one or two and
R₁ is hydrogen, C₁–C₄alkyl, phenylthio or tolylthio, in free form or in salt form, can be used as pesticides and can be prepared in a manner known per se.

22 Claims, No Drawings

CARBOXYLIC ACID DERIVATIVES

CARBOXYLIC ACID DERIVATIVES

The present invention relates to novel derivatives of ω-halovinylalkanecarboxylic acids, to processes and intermediates for their preparation, to pesticides comprising these compounds, and to their use in pest control.

ω-halovinylalkanecarboxylic acid derivatives according to the invention are those of the formula

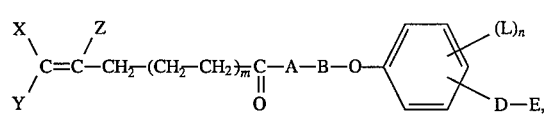 (I)

in which
A is oxygen, sulfur or —NR$_1$—;
B is C$_2$–C$_6$alkylene,
D-E is —O—E, —S—E, —O—CH$_2$—E, —O—C(=O)—E, —O—C(=O)—O—E, —O—C(=O)—N(H)—E or —O—C(=S)—N(H)—E;
E is phenyl; phenyl which is substituted by one to three substituents selected from the group, consisting of halogen, C$_1$–C$_4$alkyl, halo-C$_1$–C$_4$alkyl, C$_1$–C$_4$alkoxy, halo-C$_1$–C$_4$-alkoxy, cyano, nitro and methylenedioxy; a five-membered aromatic heterocycle which has one to three hetero atoms selected from the group, consisting of nitrogen, oxygen and sulfur; a five-membered aromatic heterocycle which has one to three hetero atoms selected from the group, consisting of nitrogen, oxygen and sulfur, and which is substituted by one or two substituents selected from the group, consisting of halogen, C$_1$–C$_4$alkyl and C$_1$–C$_4$haloalkyl; a six-membered aromatic heterocycle which has one to three nitrogen atoms; or a six-membered aromatic heterocycle which has one to three nitrogen atoms and which is substituted by one or two substituents selected from the group, consisting of halogen, C$_1$–C$_4$alkyl and C$_1$–C$_4$haloalkyl;
L is halogen or methyl;
X is fluorine;
Y is chlorine or fluorine;
Z is hydrogen, fluorine or methyl;
m is the number zero, one, two, three, four or five;
n is the number zero, one or two and
R$_1$ is hydrogen, C$_1$–C$_4$alkyl, phenylthio or tolylthio, in free form or, where appropriate, in salt form.

EP-A-0 432 861 proposes the use of halo-olefin derivatives as active ingredients in pesticides. However, the biological properties of the compounds described in this publication are not entirely satisfactory in the field of pest control, which is why there is a demand for providing other compounds having pesticidal properties, this object being achieved according to the invention by providing the present compounds I.

If appropriate, i.e. if there is at least one basic centre in the particular compound I, the compounds I according to the invention also embrace acid addition salts, in particular agrochemically acceptable acid addition salts. Examples of suitable (inorganic or organic) acids are hydrochloric acid, hydrobromic acid, sulfuric acid, phosphoric acid, nitric acid, acid which has the same central atom but whose oxidation level is higher or lower, such as perchloric acid, nitrous acid or phosphorous acid, acetic acid and succinic acid.

Unless otherwise defined, the general terms used hereinabove and hereinafter are as defined below.

The halogen atoms which are suitable as substituents are fluorine and chlorine as well as bromine and iodine, fluorine and chlorine being preferred. Halogen in this context is to be understood as meaning a substituent in its own right or part of a substituent, such as in haloalkyl or haloalkoxy.

Carbon-containing groups and compounds comprise, unless otherwise defined, in each case preferably 1 up to and including 4, particularly 1 or 2, carbon atoms.

The alkyl and alkoxy radicals which are suitable as substituents can be straight-chain or branched. Examples of such alkyl radicals which may be mentioned are methyl, ethyl, propyl, isopropyl, butyl, isobutyl, sec-butyl or tert-butyl. Suitable alkoxy radicals which may be mentioned are, inter alia, methoxy, ethoxy, propoxy, isopropoxy or butoxy and their isomers.

If the alkyl, alkoxy or phenyl groups or aromatic heterocycles which are suitable as substituents are substituted by halogen, they can be only partially halogenated or else perhalogenated. The definitions given above for halogen, alkyl and alkoxy apply in this case. Examples of the alkyl elements of these groups are methyl which is mono- to trisubstituted by fluorine, chlorine and/or bromine, such as CHF$_2$ or CF$_3$; ethyl which is mono- to pentasubstituted by fluorine, chlorine and/or bromine, such as CH$_2$CF$_3$, CF$_2$CF$_3$, CF$_2$CCl$_3$, CF$_2$CHCl$_2$, CF$_2$CHF$_2$, CF$_2$CFCl$_2$, CF$_2$CHBr$_2$, CF$_2$CHClF, CF$_2$CHBrF or CClFCHClF; propyl or isopropyl, each of which is mono- to heptasubstituted by fluorine, chlorine and/or bromine, such as CH$_2$CHBrCH$_2$Br, CF$_2$CHFCF$_3$, CH$_2$CF$_2$CF$_3$ or CH(CF$_3$)$_2$; and butyl or an isomer thereof, each of which is mono- to nonasubstituted by fluorine, chlorine and/or bromine, such as CF(CF$_3$)CHFCF$_3$ oder CH$_2$(CF$_2$)$_2$CF$_3$. The aromatic heterocycles carry the substituents which are possible preferably on one of the carbon atoms which together with the hetero atoms form the ring skeleton. As a rule, these rings are also bonded to the bridging member D via a carbon atom of the ring. The five-membered aromatic heterocycles of the definition according to the invention of the radical E are preferably the following basic structures: pyrrole, imidazole, pyrazole, 1,2,3-triazole, 1,2,4-triazole, oxazole, isoxazole, thiazole, isothiazole, 1,2,3-thiadiazole, 1,2,4-thiadiazole, 1,3,4-thiadiazole, 1,2,3-oxadiazole, 1,2,4-oxadiazole and 1,3,4oxadiazole. Six-membered aromatic heterocycles which are suitable for E are, according to the invention, pyridine, pyrimidine, pyrazine, pyridazine, 1,2,4-triazine and 1,3,5-triazine. If these aromatic radicals which have been defined under E as well as phenyl are further substituted, they can be mono- to trisubstituted by identical or different substituents from those listed. The substituted aromatic substituents preferably have one to two substituents. In particular, the aromatic radicals of definition -D-E also have the following, individualised meanings:
phenoxy,
phenylthio,
3,5-dichloropyrid-2-yloxy,
pyrid-2-yloxy,
benzyloxy,
3-chlorophenoxy,
3-methyl-1,2,4-thiadiazol-5-yloxy,
4-fluorophenoxy,
3-fluorophenoxy,
2-fluorophenoxy,
3-chloro-5-trifluoromethyl-pyrid-2-yloxy,
3-chloro-5-(2,2-dichloro-1,1,2-trifluoro-ethyl)-pyrid-2-yloxy,
3,5-difluorophenoxy,
2-ethoxymethyl-1,3,4-thiadiazol-5-ylmethoxy, 3-isopropyl-1,2,4-thiadiazol-5-yloxy,
4-chlorophenoxy,
2-chloro-4-trifluoromethyl-phenoxy,
5-bromothien-2-ylmethoxy,
4-trifluoromethylphenoxy,
4-ethylphenoxy,
4-methoxyphenoxy,
4-chlorophenylthio and
4-chlorobenzyloxy,
4-cyanobenzyloxy,
2-nitrobenzyloxy,
3-nitrobenzyloxy,
4-nitrobenzyloxy,
4-fluorobenzyloxy,
4-trifluoromethylbenzyloxy,
4-methylbenzyloxy,
4-methoxybenzyloxy
4-t-butylbenzyloxy,
4-t-butylphenoxy.

The radicals -D-E can occupy the ortho, meta or para position of the phenyl radical. The para position is preferred.

Due to the obligatory ω position of the vinyl group in the basic alkenylcarboxylic acid, the definition of the formula I embraces derivatives of but-3-enoic acid, hex-5-enoic acid, oct-7-enoic acid, dec-9-enoic acid, dodec-11-enoic acid and tetradec-1 3-enoic acid.

Sub-groups from the compounds of the formula I which must be emphasised are those in which either a) A is oxygen, or
b) B is an ethylene bridge, or
c) A is a bridge —NH—, or
d) n is the number zero, or
e) D is —O—, or
f) E is phenyl, pyridyl, thiadiazolyl, phenyl which is substituted by one or two substituents selected from the group, consisting of cyano, nitro, halogen, $C_1$–$C_4$alkyl and $C_1$–$C_4$haloalkyl, pyridyl which is substituted by one or two substituents selected from the group, consisting of halogen, $C_1$–$C_4$alkyl and halo-$C_1$–$c_4$alkyl, or $C_1$–$C_4$alkylthiazolyl, or
g) m is the number zero, one or four, or
h) Y is fluorine and Z is hydrogen, or
i) D is —O—$CH_2$—, or
k) D is —O—CO— or —O—CO—O—.

Preferred compounds from amongst those of sub-group a) are those in which n is zero, in particular those in which n is zero and m is zero, one or four, very particularly those in which n is zero, m is zero, one or four and B is an ethylene bridge.

Other preferred compounds from amongst those of sub-group a are those in which n is zero and D is oxygen or sulfur, in particular those in which n is zero, D is oxygen or sulfur and B is an ethylene bridge, very particularly preferably those in which n is zero, D is oxygen or sulfur, B is an ethylene bridge and m is zero, one or four.

Other preferred compounds from amongst those of sub-group a) are those in which D is —O—$CH_2$—, in particular those in which D is —O—$CH_2$, n is zero and B is an ethylene bridge, very particularly preferably those in which D is —O—$CH_2$—, n is zero, B is an ethylene bridge and m is zero, one or four.

Other preferred compounds from amongst those of sub-group a) are those in which D is the group —O—CO— or —O—CO—O—, in particular those in which D is the group —O—CO— or —O—CO—O— and n is zero, particularly preferably those in which D is the group —O—CO— or —O—CO—O—, n is zero, B is an ethylene bridge and m is zero, one or four.

Preferred compounds from amongst those of sub-group c) are those in which E is a substituted or unsubstituted phenyl, thiadiazolyl or pyridyl group, in particular those in which E is phenyl, cyanophenyl, nitrophenyl, chlorophenyl, fluorophenyl, methylphenyl, t-butylphenyl, methoxyphenyl, trifluoromethylphenyl, methylthiadiazolyl, pyridyl, chloropyridyl, trifluoromethylpyridyl or chlorotrifluoromethylpyridyl.

Preferred compounds from amongst those of sub-group f) are those in which D is —O—$CH_2$—.

Other preferred compounds from amongst those of sub-group t) are those in which D is oxygen.

Other preferred compounds from amongst those of sub-group f) are those in which D is oxygen or —O—$CH_2$—, Y is fluorine and Z is hydrogen, in particular those in which D is oxygen or —O—$CH_2$—, Y is fluorine, Z is hydrogen and n is zero, very particularly those in which D is oxygen or —O—$CH_2$—, Y is fluorine, Z is hydrogen, n is zero and B is an ethylene bridge.

Other preferred compounds from amongst those of sub-group f) are those in which E is phenyl, cyanophenyl, nitrophenyl, chlorophenyl, fluorophenyl, methylphenyl, t-butylphenyl, methoxyphenyl, trifluoromethylphenyl, methylthiadiazolyl, pyridyl, chloropyridyl, trifluoromethylpyridyl or chlorotrifluoromethylpyridyl, in particular those in which D is, on the one hand, oxygen or, on the other hand, the group —O—$CH_2$—.

Very particularly preferred compounds of the formula I are those in which A is oxygen, B is an ethylene bridge, n is the number zero, D is oxygen, sulfur or —O—$CH_2$—, E is phenyl, pyridyl, thiadiazolyl, phenyl which is substituted by one or two substiments selected from the group, consisting of cyano, nitro, halogen, $C_1$–$C_4$alkyl and $C_1$–$C_4$haloalkyl, pyridyl which is substituted by one or two substituents selected from the group, consisting of halogen, $C_1$–$C_4$alkyl and halo-$C_1$–$C_4$alkyl, or $C_1$–$C_4$alkylthiazolyl, m is the number zero, one or four, Y is fluorine and Z is hydrogen.

From amongst those preferred compounds of the formula I, those in which either A is oxygen, B is an ethylene bridge, D is oxygen, sulfur or —O—$CH_2$—, m is the number zero, one or four, n is the number zero, Y is fluorine and Z is hydrogen; or in which A is —NH—, B is an ethylene bridge, D is oxygen or sulfur, m is the number zero, one or four, n is the number zero, Y is fluorine and Z is hydrogen, are particularly distinguished by their good activity.

The following may be mentioned as preferred individual compounds of the formula I according to the invention:
2-(4-phenoxyphenoxy)ethyl 4,4-difluorobut-3-enoate,
2-(4-benzyloxyphenoxy)ethyl 4,4-difluorobut-3-enoate,
2-[4-(4-methyl)benzyloxyphenoxy]ethyl 4,4-difluorobut-3-enoate,
2-(4-phenoxyphenoxy)ethyl 6,6-difluorohex-5-enoate,
2-(4-benzyloxyphenoxy)ethyl 6,6-difluorohex-5-enoate,
2-(4-phenoxyphenoxy)ethyl 8,8-difluorooct-7-enoate,
2-(4-benzyloxyphenoxy)ethyl 8,8-difluorooct-7-enoate,
2-(4-phenoxyphenoxy)ethyl 10,10-difluorodec-9-enoate,
2-(4-benzyloxyphenoxy)ethyl 10,10-difluorodec-9-enoate,
2-(4-phenoxyphenoxy)ethyl 12,12-difluorododec-11-enoate, and
2-(4-benzyloxyphenoxy)ethyl 12,12-difluorododec-11-enoate.

The invention furthermore relates to a process for the preparation of the compounds of the formula I, in free form or, where appropriate, in salt form, which comprises, for example, a) reacting a compound of the formula

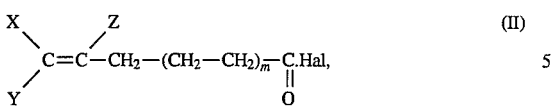

in which X, Y, Z and m are as defined in formula I and Hal is chlorine or bromine, with a compound of the formula

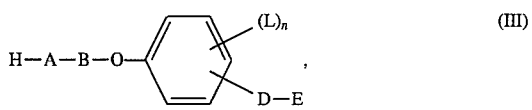

in which A, B, L, D, E and n are as defined in formula I or, where appropriate, a salt thereof, in the presence or absence of an inert solvent and in the presence of an acid-binding agent, or b) reacting a compound of the formula

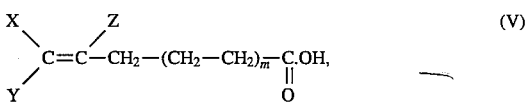

in which X, Y, Z and m are as defined in formula I, with a compound of the formula III or, where appropriate, a salt thereof, in the presence or absence of an inert solvent and of a catalyst or a dehydrating agent, and in each case, if desired, converting a free compound of the formula I which can be obtained according to the process into a salt, or converting a salt of a compound of the formula I, which can be obtained according to the process, into the free compound of the formula I or into a different salt.

The reaction of process a) is preferably effected in an inert hydroxyl-free solvent in the presence of an organic base, for example pyridine, 4-dimethylaminopyridine, lutidine, collidine, trialkylamine, N,N-dialkylaniline, or a bicyclic, non-nucleophilic base, such as 1,4-diazabicyclo[2.2.2]octane (DABCO), 1,5-diazabicyclo[4.3.0]non-5-ene (DBN) or 1,8-diazabicyclo[5.4.0]undec-7-ene (1,5-5) (DBU). As a rule, the reaction is carried out at temperatures from −30° C. to +70° C., preferably from −10° C. to +50° C. It is expedient to carry out the process in the presence of a solvent or solvent mixture which is inert to the reaction. Suitable for this purpose are, for example, aliphatic and aromatic hydrocarbons such as benzene, toluene, xylenes, petroleum ether or hexane; halogenated hydrocarbons such as chlorobenzene, methylene chloride, ethylene chloride, chloroform, carbon tetrachloride or tetrachloroethylene; ethers and ether-like compounds such as dialkyl ethers (diethyl ether, diisopropyl ether, tert-butyl methyl ether, etc.), anisole, dioxane, tetrahydrofuran; nitriles such as acetonitrile or propionitrile; esters such as ethyl acetate, propyl acetate or butyl acetate; ketones such as acetone, diethyl ketone, methyl ethyl ketone; and mixtures of such solvents with each other. Alternatively, the reaction can be carried out using an excess of one of the abovementioned bases or, in the event that the compound of the formula III is an amine (A=NR$_1$), a second equivalent or a larger excess of the compound of the formula III can also be used instead of the base. The reaction is carried out under ambient pressure, even though it could also be carried out under elevated or reduced pressure.

In process variant b), the reaction is advantageously carried out in the presence of dehydrating reagents conventionally used for esterification reactions, for example in the presence of a carbodiimide [dicyclohexylcarbodiimide (DCC)] or of a 1-alkyl-2-halopyridinium salt such as 1-methyl-2-chloropyridinium iodide. The reaction is then advantageously carried out at temperatures from −30° C. to +70° C., preferably −10° C. to +50° C., in the presence of a solvent or solvent mixture which is inert to the reaction. The process is preferably carried out in the presence of a base, for example in the presence of an organic amine, such as a trialkylamine (trimethylamine, triethylamine, tripropylamine or diisopropylethylamine), of a pyridine (pyridine as such, 4-dimethylaminopyridine or 4-pyrrolidinopyridine), of a morpholine (N-methylmorpholine) or of an N,N-dialkylaniline (N,N-dimethylaniline or N-methyl-N-ethylaniline). Examples of suitable solvents are aliphatic and aromatic hydrocarbons such as benzene, toluene, xylenes, petroleum ether or hexane; halogenareal hydrocarbons such as chlorobenzene, methylene chloride, ethylene chloride, chloroform, carbon tetrachloride or tetrachloroethylene; ethers and ether-like compounds such as dialkyl ethers (diethyl ether, diisopropyl ether, tert-butyl methyl ether, etc.), anisole, dioxane or tetrahydrofuran; nitriles such as acetonitrile or propionitrile; esters such as ethyl acetate, propyl acetate or butyl acetate; and mixtures of such solvents with each other.

If the compound of the formula III is an alcohol (A=O), then process variant b) can also be carried out in the presence of an acid catalyst, for example H$_2$SO$_4$, HCl or a sulfonic acid such as methanesulfonic acid or p-toluenesulfonic acid. The process is advantageously carded out using an excess of the alcohol of the formula III. In this process, water which is liberated can be removed continuously from the reaction mixture. A conventionally used method is removal of the reaction product water by distilling off an azeotropic mixture of the solvent with water. Solvents which are suitable for this purpose are benzene, toluene, xylene, methylene chloride or chloroform.

The conversion of free compounds I into salts, and of salts into free compounds I or into other salts, is effected, for example, by treating a free compound I with an acid, or by treating a salt with a base.

Basically, the various derivatives of the formula I can also be obtained by transesterification or amidation from the lower alkyl esters of the co-halovinylalkanecarboxylic acid of the formula V.

For example, the ester-type derivatives of the formula I (A=O or S) can be obtained by base- or acid-catalysed transesterification of the lower alkyl esters of the formula

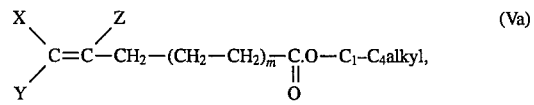

in which X, Y, Z and m are as defined in formula I, with the alcohols or mercaptans of the formula

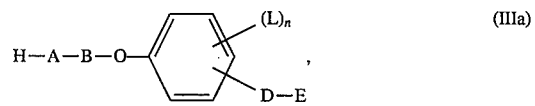

in which B, D, E, L and n are as defined in formula I and A is oxygen or sulfur. Particularly suitable acid catalysts are HCl, H$_2$SO$_4$ or a sulfonic acid. The preferred base for the base-catalysed transesterification is the sodium alcoholate or potassium alcoholate of the alcohol or mercaptan of the formula IIIa, which is accessible from IIIa, for example, by an addition of sodium hydride or potassium hydride. The transesterification reaction is preferably carried out at temperatures between −20° C. and +120° C., in particular between 0° C. and +100° C. It is advantageous to use an excess of the alcohol or mercaptan component IIIa. Suitable solvents are ethers such as diethyl ether, diisopropyl ether, dioxane or tetrahydrofuran, halogenated hydrocarbons or aliphatic or aromatic hydrocarbons.

Amide-type derivatives of the formula I (A=NR$_1$) are obtained from the lower alkyl esters of the formula Va by reacting them with an amine of the formula

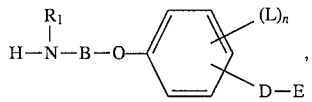         (IIIb)

in which R$_1$, B, D, E, L and n are as defined in formula I, or a salt thereof. The amidation reactions are carried out at temperatures between 0° C. and +120° C. The reactants are reacted advantageously in an inert solvent or solvent mixture. These are, for example, aliphatic and aromatic hydrocarbons such as benzene, toluene, xylenes, petroleum ether or hexane; halogenated hydrocarbons such as chlorobenzene, methylene chloride, ethylene chloride, chloroform, carbon tetrachloride or tetrachloroethylene; ethers and ether-type compounds such as dialkyl ethers (diethyl ether, diisopropyl ether, tert-butyl methyl ether, etc.), anisole, dioxane or tetrahydrofuran; nitriles such as acetonitrile or propionitrile; alcohols such as methanol, ethanol, propanol or isopropanol; or water. It is advantageous to use an excess of the amine combponent IIIb.

The compounds of the formulae II, III, IIIa, IIIb, V and Va and their preparation are known from the literature. The compounds II and V can be prepared by the processes described in U.S. Pat. No. 4,950,666 and EP-A-0 432 861. The reaction conditions for the synthesis of the free acid from an ester and the subsequent facultative conversion of this acid V into the acid halide of the formula II correspond to the conventional conditions for an acid- or base-catalysed hydrolysis, or for a halogenation of a carboxylic acid. The compounds of the formulae III, IIIa and IIIb, which have previously not been described in the literature, can be obtained analogously to the known processes by customary synthesis methods.

A further process allows those compounds of the formula I in which Z is hydrogen or methyl to be obtained in free form or in salt form by reacting an ω-carbonylalkanecarboxylic acid derivative of the formula

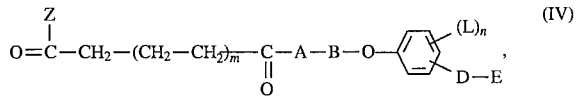         (IV)

in which A, B, L, D, E, m and n am as defined in formula I and Z is hydrogen or methyl or, where appropriate, a salt thereof, with a halomethane such as CF$_2$Br$_2$, CCl$_2$F$_2$ or CCl$_3$F, or an alkaline trihaloacetate such as ClF$_2$C—CO—ONa or Cl$_2$FC—CO—ONa, in an inert solvent in the presence of a trisubstituted phosphane, such as P(C$_6$H$_5$)$_3$, P(C$_2$H$_5$)$_3$, P[N(C$_2$H$_5$)$_2$]$_3$ or P[N(CH$_3$)$_2$]$_3$.

Particularly suitable solvents for carrying out this reaction variant are ethers such as diglyme, triglyme or tetraglyme, or dimethylacetamide. As a rule, this reaction step is carried out at a temperature of between 0° C. and +150° C., preferably between +20° C. and +100° C.

The compounds of the formula IV and, where appropriate, salts thereof, are novel. They were developed specifically for synthesising the active ingredients of the formula I. The compounds of the formula IV are therefore part of the present invention.

The compounds of the formula IV can be prepared by processes known per se from products which have been described in the literature or which are commercially available. For example, a compound of the formula IV can be prepared by reacting an acid or an acid halide of the formula

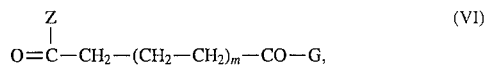         (VI)

in which m is as defined in formula I, G is hydroxyl or halogen, preferably chlorine or bromine, and Z is hydrogen or methyl, with a compound of the formula III or, where appropriate, a salt thereof, in the presence or absence of an inert solvent and of a catalyst or a dehydrating agent. The reaction conditions of this esterification or amidation correspond to those of process variants a) and b).

The compounds of the formula VI are known or can be prepared analogously to known processes.

A further process allows the compounds of the more specific sub-group of the formula

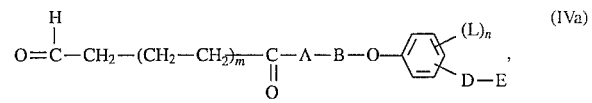         (IVa)

in which A, B, D, E, L, m and n are as defined in formula I and, where appropriate, salts thereof, to be obtained by heating an ω-haloalkanecarboxylic acid derivative of the formula

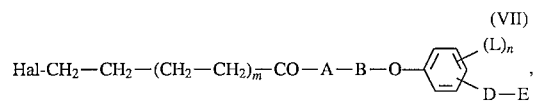         (VII)

in which A, B, D, E, L, m and n are as defined in formula I and Hal is chlorine, bromine or iodine, or, where appropriate, a salt thereof, in dimethyl sulfoxide. The temperatures in this reaction are preferably between +50° C. and +180° C.

The compounds of the formula VII can be obtained, for example, from a compound of the formula

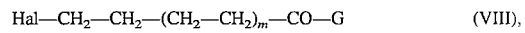         (VIII), in which m is as defined in formula I, G is hydroxyl or halogen, preferably chlorine or bromine, and Hal is chlorine, bromine or iodine, by esterification or amidation analogous to process variants a) and b).

The compounds of the formula VIII are known or can be prepared analogously to known processes.

Compounds of the formula I in which Y is chlorine can exist as double-bond isomers in the E or Z form. The pure double-bond isomers can be separated from the isomer mixture with the aid of physical methods such as distillation or solid/liquid chromatography.

The compounds I according to the invention are valuable active ingredients in the field of pest control while being well tolerated by warm-blooded species, fish and plants. The active ingredients according to the invention are active, in particular, against insects and arachnids which can be found on useful plants and ornamentals in agriculture and horticulture, in particular in crops of rice, cotton, vegetables and fruit, and in forests. The compounds I are particularly suitable for controlling insects in crops of rice, fruit and vegetables, in particular plant-injurious insects such as

*Aphis craccivora, Nilaparvata lugens* and *Nephotettix cincticeps*. Other fields of application for the active ingredients according to the invention are the protection of stored products and materials and, in the hygiene sector, in particular the protection of domestic animals and productive livestock. The compounds I are active against all or individual development stages of normally sensitive, but also resistant, pest species. Their activity becomes apparent, for example, from a destruction of the pests, either immediately or only after some time has elapsed, for example during moulting, or from reduced oviposition and/or hatching rates.

The abovementioned pests include:

from the order Lepidoptera, for example Acleris spp., Adoxophyes spp., Aegeria spp., Agrotis spp., *Alabama argillaceae*, Amylois spp., *Anticarsia gemmatalis*, Archips spp., Argyrotaenia spp., Autographa spp., *Busseola fusca, Cadra cautella, Carposina nipponensis,* Chilo spp., Choristoneura spp., *Clysia ambiguella,* Cnaphalocrocis spp., Cnephasia spp., Cochylis spp., Coleophora spp., *Crocidolomia binotalis, Cryptophlebia leucotreta,* Cydia spp., Diatraea spp., *Diparopsis castanea,* Earias spp., Ephestia spp., Eucosma spp., *Eupoecilia ambiguella,* Euproctis spp., Euxoa spp., Grapholita spp., *Hedya nubiferana,* Hellothis spp., *Hellula undalis, Hyphantria cunea, Keiferia lycopersicella, Leucoptera scitella,* Lithocollethis spp., *Lobesia botrana,* Lymantria spp., Lyonefta spp., Malacosoma spp., *Mamestra brassicae, Manduca sexta,* Operophtera spp., *Ostrinia nubilalis,* Pammene spp., Pandemis spp., *Panolis flammea, Pectinophora gossypiella, Phthorimaea operculella, Pieris rapae,* Pieris spp., *Plutella xylostella,* Prays spp., Scirpophaga spp., Sesamia spp., Sparganothis spp., Spodoptera spp., Synanthedon spp., Thaumetopoea spp., Tortrix spp., *Trichoplusia ni* and Yponomeuta spp.;

from the order Coleoptera, for example Agriotes spp., Anthonomus spp., *Atomaria linearis, Chaetocnema tibialis,* Cosmopolites spp., Curculio spp., Demiestes spp., Diabrotica spp., Epilachna spp., Eremnus spp., *Leptinotarsa decemlineata,* Lissorhoptrus spp., Melolontha spp., Orycaephilus spp., Otiorhynchus spp., Phlyctinus spp., Popillia spp., Psylliodes spp., Rhizopertha spp., Scarabeidae, Sitophilus spp., Sitotroga spp., Tenebrio spp., Tribolium spp. and Trogoderma spp.;

from the order Orthoptera, for example Blatta spp., Blattella spp., Gryllotalpa spp., *Leucophaea maderae,* Locusta spp., Periplaneta spp. and Schistocerca spp.;

from the order Isoptera, for example Reticulitemes spp.;

from the order Psocoptera, for example Liposcelis spp.;

from the order Anoplura, for example Haematopinus spp., Linognathus spp., Pediculus spp., Pemphigus spp. and Phylloxera spp.;

from the order Mallophaga, for example Damalinea spp. and Trichodectes spp.;

from the order Thysanoptera, for example Frankliniella spp., Hercinothrips spp., Taeniothrips spp., *Thrips palmi, Thrips tabaci* and *Scirtothrips aurantii;* from the order Heteroptera, for example Cimex spp., *Distantiella theobroma,* Dysdercus spp., Euchistus spp., Eurygaster spp., Leptocorisa spp., Nezara spp., Piestoa spp., Rhodnius spp., *Sahlbergella singularis,* Scotinophara spp. and Triatoma spp.;

from the order Homoptera, for example *Aleurothrixus floccosus, Aleyrodes brassicae,* Aonidiella spp., Aphididae, Aphis spp., Aspidiotus spp., *Bemisia tabaci,* Ceroplaster spp., *Chrysomphalus aonidium, Chrysomphalus dictyospermi, Coccus hesperidum,* Empoasca spp., *Eriosoma larigerum,* Erythroneura spp., Gascardia spp., Laodelphax spp., *Lecanium corni,* Lepidosaphes spp., Macrosiphus spp., Myzus spp., Nephotettix spp., Nilaparvata spp., Paratoria spp., Pemphigus spp., Planococcus spp., Pseudaulacaspis spp., Pseudococcus spp., Psylla spp., *Pulvinaria aethiopica,* Quadraspidiotus spp., Rhopalosiphum spp., Saissetia spp., Scaphoideus spp., Schizaphis spp., Sitobion spp., *Trialeurodes vaporariorum, Trioza erytreae* and *Unaspis citri;* from the order Hymenoptera, for example Acromyrmex, Alta spp., Cephus spp., Diprion spp., Diprionidae, *Gilpinia polytoma,* Hoplocampa spp., Lasius spp., *Monomorium pharaonis,* Neodiprion spp., Solenopsis spp. and Vespa spp.;

from the order Diptera, for example Aedes spp., *Antherigona soccata, Bibio hortulanus, Calliphora erythrocephala,* Ceratitis spp., Chrysomyia spp., Culex spp., Cuterebra spp., Dacus spp., *Drosophila melanogaster,* Fannia spp., Gastrophilus spp., Glossina spp., Hypoderma spp., Hyppobosca spp., Liriomyza spp., Lucilia spp., Melanagromyza spp., Musca spp., Oestrus spp., Orseolia spp., *Oscinella frit, Pegomyia hyoscyami,* Phorbia spp., *Rhagoletis pomonella,* Sciara spp., Stomoxys spp., Tabanus spp., Tannia spp. and Tipula spp.;

from the order Siphonaptera, for example Ceratophyllus spp. and *Xenopsylla cheopis;* from the order Thysanura, for example *Lepisma saccharina* and from the order Acarina, for example *Acarus siro, Aceria sheldoni, Aculus schlechtendali,* Amblyomma spp., Argas spp., Boophilus spp., Brevipalpus spp., *Bryobia praetiosa,* Calipitrimerus spp., Chorioptes spp., *Dermanyssus gallinae, Eotetranychus carpini,* Eriophyes spp., Hyalomma spp., Ixodes spp., *Olygonychus pratensis,* Ornithodoros spp., Panonychus spp., *Phyllocoptruta oleivora, Polyphagotarsonemus latus,* Psoroptes spp., Rhipicephalus spp., Rhizoglyphus spp., Sarcoptes spp., Tarsonemus spp. and Tetranychus spp..

The compounds of the formula I are particularly suitable for controlling pests in crops of cotton, vegetables, fruit and rice, such as spider mites, aphids, caterpillars and plant- and leaf-hoppers in rice. This allows mainly spider mites such as *Panonychus ulmi,* aphids such as *Aphis craccivora,* caterpillars such as those of *Heliothis virescens* and plant- and leaf-hoppers in rice such as *Nilaparvata lugens* or *Nephotettix cincticeps* to be controlled.

The good pesticidal activity of the compounds I according to the invention corresponds to a mortality rate of at least 50–60% of the abovementioned pests.

The activity of the compounds I according to the invention and of the compositions containing them can be broadened considerably and adapted to prevailing circumstances by adding other insecticides and/or acaricides. Representatives of the following active ingredient classes are examples of suitable additives: organophosphorus compounds, nitrophenols and derivatives, formamidines, ureas, carbamates, pyrethroids, chlorinated hydrocarbons and Bacillus thuringiensis preparations.

The compounds of the formula I are employed as pure active ingredients or, preferably, together with the auxiliaries conventionally used in the art of formulation, and they can therefore be processed in a known manner to give, for example, emulsifiable concentrates, directly sprayable or dilutable solutions, dilute emulsions, wettable powders, soluble powders, dusts, granules and also encapsulations in polymeric substances. The methods of application, such as spraying, atomising, dusting, scattering or pouring, as well as the compositions are selected to suit the intended aims and the prevailing circumstances.

The formulations, i.e. the compositions, preparations or combinations comprising the active ingredient of the formula I, or combinations of these active ingredients with other insecticides or acaricides, with or without a solid or liquid additive, are prepared in a known manner, for example by intimately mixing and/or grinding the active ingredients with extenders, for example solvents, solid carriers and, if appropriate, surface-active compounds (surfactants).

The following are suitable as solvents: aromatic hydrocarbons, preferably the fractions $C_8$ to $C_{12}$ of alkylbenzenes such as xylene mixtures or alkylated naphthalenes, aliphatic or cycloaliphatic hydrocarbons, such as cyclohexane, paraffins or tetrahydronaphthalene, alcohols such as ethanol, propanol or butanol, and glycols as well as their ethers and esters, such as propylene glycol, dipropylene glycol ether, ethylene glycol, ethylene glycol monomethyl ether or ethylene glycol monoethyl ether, ketones such as cyclohexanone, isophorone or diacetanol alcohol, strongly polar solvents such as N-methyl-2-pyrrolidone, dimethyl sulfoxide or dimethylformamide, or water, vegetable oils such as rapeseed oil, castor oil, coconut oil or soya oil; if appropriate, also silicone oils.

Solid carriers which are used, for example, for dusts and dispersible powders are, as a rule, natural ground minerals such as calcite, talc, kaolin, montmorillonite or attapulgite. To improve the physical properties, it is also possible to add highly-disperse silica or highly-disperse absorptive polymers. Possible particulate, adsorptive carriers for granules are either porous types, for example pumice, brick grit, sepiolite or bentonite, or non-sorptive carrier materials, for example calcite or sand. Moreover, a large number of granulated materials of inorganic or organic nature can be used such as, in particular, dolomite or comminuted plant residues.

Suitable surface-active compounds are non-ionic, cationic and/or anionic surfactants which have good emulsifying, dispersing and wetting properties, depending on the nature of the active ingredient of the formula I to be formulated or of the combinations of these active ingredients with other insecticides or acaricides. Surfactants are also to be understood as meaning surfactant mixtures.

Suitable anionic surfactants can be either so-called water-soluble soaps or water-soluble, synthetic surface-active compounds.

Soaps which are suitable are the alkali metal salts, alkaline earth metal salts or substituted or unsubstituted ammonium salts of higher fatty acids ($C_{10}$–$C_{22}$) such as the sodium salts or potassium salts of oleic or stearic acid, or of natural mixtures of fatty acids which can be obtained from, for example, coconut oil or tall oil. Other surfactants which may be mentioned are the fatty acid methyltaurinates.

However, so-called synthetic surfactants am used more frequently, in particular fatty sulfonates, fatty sulfates, sulfonated benzimidazole derivatives or alkylarylsulfonates.

The fatty sulfonates or fatty sulfates are, as a rule, in the form of alkali metal salts, alkaline earth metal salts or substituted or unsubstituted ammonium salts and have, as a rule, an alkyl radical having 8 to 22 carbon atoms, alkyl also including the alkyl moiety of acyl radicals, for example the sodium salt or calcium salt of ligninsulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives comprise preferably 2 sulfonyl groups and a fatty acid radical having approximately 8–22 carbon atoms. Alkylarylsulfonates are, for example, the sodium salts, calcium salts or triethanolamine salts of dodecylbenzenesulfonic acid, of dibutylnaphthalenesulfonic acid or of a naphthalenesulfonic acid/formaldehyde condensation product. Suitable phosphates, for example salts of the phosphoric ester of a p-nonylphenol/(4–14)ethylene oxide adduct, or phospholipids, are also suitable.

Suitable non-ionic surfactants are mainly polyglycol ether derivatives of aliphatic or cycloaliphatic alcohols, saturated or unsaturated fatty acids and alkylphenols, which can comprise 3 to 30 glycol ether groups and 8 to 20 carbon atoms in the (aliphatic) hydrocarbon radical and 6 to 18 carbon atoms in the alkyl radical of the alkylphenols. Other suitable non-ionic surfactants are the water-soluble polyethylene oxide adducts with polypropylene glycol, ethylene diaminopolypropylene glycol and alkyl polypropylene glycol which have 1 to 10 carbon atoms in the alkyl chain and comprise 20 to 250 ethylene glycol ether groups and 10 to 100 propylene glycol ether groups. The abovementioned compounds customarily comprise 1 to 5 ethylene glycol units per propylene glycol unit.

Examples of non-ionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Other substances which are suitable are fatty acid esters of polyoxyethylene sorbitan, such as polyoxyethylene sorbitan trioleate.

The cationic surfactants are mainly quatern,try ammonium salts which comprise, as N substituent, at least one alkyl radical having 8 to 22 carbon atoms and as further substituents lower, halogenated or unhalogenated alkyl, benzyl or lower hydroxyalkyl radicals. The salts are preferably in the form of halides, methylsulfates or ethylsulfates, for example stearyltrimethylammonium chloride or benzyldi(2-chloroethyl)ethylammonium bromide.

The abovementioned surfactants are only to be regarded as examples; a large number of other surfactants conventionally used in the art of formulation and suitable according to the invention are described in the specialist literature.

As a rule, the pesticidal preparations comprise 0.1 to 99%, in particular 0.1 to 95%, of active ingredient I or a combination of this active ingredient with other insecticides and/or acaricides, and 1 to 99.9%, in particular 5 to 99.9%, of a solid or liquid auxiliary, it being possible, as a rule, for 0 to 25%, in particular 0.1 to 20%, of the preparations to be surfactants (% in each case meaning per cent by weight). While concentrated compositions are more preferred as commercially available goods, the end consumer uses, as a rule, dilute preparations with considerably lower concentrations of active ingredients. Typical use concentrations are between 0.1 and 1000 ppm, preferably between 0.1 and 500 ppm. The rates of application per hectare are, as a rule, 1 to 1000 g of active ingredient per hectare, preferably 25 to 500 g/ha.

Preferred formulations have, in particular, the following composition (%=per cent by weight):
Emulsifiable concentrates:
Active ingredient: 1 to 90%, preferably 5 to 20%
Surfactant: 1 to 30%, preferably 10 to 20%
Liquid carrier: 5 to 94%, preferably 70 to 85%
Dusts:
Active ingredient: 0.1 to 10%, preferably 0.1 to 1%
Solid carrier: 99.9 to 90%, preferably 99.9 to 99%
Suspension concentrates:
Active ingredient: 5 to 75%, preferably 10 to 50%
Water: 94 to 24%, preferably 88 to 30%

Surfactant: 1 to 40%, preferably 2 to 30%
Wettable powders:
Active ingredient: 0.5 to 90%, preferably 1 to 80%
Surfactant: 0.5 to 20%, preferably 1 to 15%
Solid carrier: 5 to 95%, preferably 15 to 90%
Granules:
Active ingredient: 0.5 to 30%, preferably 3 to 15%
Solid carrier: 99.5 to 70%, preferably 97 to 85%

The preparations can also comprise other auxiliaries such as stabilisers, for example epoxidised or unepoxidised vegetable oils (for example epoxidised coconut oil, rapeseed oil or soya oil), antifoams, for example silicone oil, preservatives, viscosity regulators, binders and/or tackifiers, as well as fertilisers or other active ingredients for achieving specific effects.

The examples which follow are intended to illustrate, but not to limit, the invention.

Temperatures are given in degrees centigrade.

PREPARATION EXAMPLES

Example H1

2-(4-phenoxyphenoxy)ethyl-4,4-difluorobut-3-enoate
(Table 1, Compound No. 1.01)

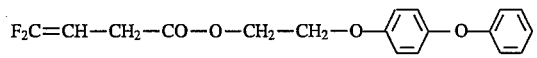

A solution of 3.0 g of 4,4-difluorobut-3-enoic acid in 50 ml of diethyl ether is treated with 0.36 g of 4-pyrrolidinopyridine and 5.66 g of 2-(4-phenoxyphenoxy)ethanol, and the mixture is cooled to 0° C. A total of 5.58 g of N,N'-dicyclohexylcarbodiimide are added in portions at a temperature of between 0° C. and +5° C., the ice-cooling is removed, and the reaction mixture is allowed to come to room temperature in the course of 16 hours, with stirring. The N,N'-dicyclohexylurea which has precipitated as a solid is separated off and discarded. The supernatant solution is evaporated. The residue obtained is purified by column chromatography on silica gel (eluent: hexane/ethyl acetate, 9:1). This gives pure 2-(4-phenoxyphenoxy)ethyl 4,4-difilorobut-3-enoate in the form of an oil (refractive index $n_D^{23}$: 1.5315).

Example H2:

The other compounds of the formula I listed in Tables 1 to 6 below can also be prepared as described in Example H1. In the column "physical data" of these tables, "m.p." represents the melting point of the compound in question, and "$n_D^T$" represents the refractive index of the compound in question at a temperature of T °C.

TABLE 1

$$F_2C=CH-CH_2-\underset{\underset{O}{\parallel}}{C}-A-R$$

| Comp. No. | R | A | Physical data |
|---|---|---|---|
| 1.01 | —CH₂—CH₂—O—⟨phenyl⟩—O—⟨phenyl⟩ | O | $n_D^{23}$:1.5315 |
| 1.02 | —CH₂—CH₂—O—⟨phenyl⟩—OCH₂—⟨phenyl⟩ | O | |
| 1.03 | —CH₂—CH₂—O—⟨phenyl⟩—OCH₂—⟨pyridyl⟩ | O | |
| 1.04 | —CH₂—CH₂—O—⟨phenyl⟩—OCH₂—⟨thiadiazole-CH₂OC₂H₅⟩ | O | |
| 1.05 | —CH₂—CH₂—O—⟨phenyl⟩—O—⟨thienyl-Br⟩ | O | |
| 1.06 | —CH₂—CH₂—O—⟨phenyl⟩—OCH₂—⟨phenyl⟩—F | O | |

TABLE 1-continued $$F_2C=CH-CH_2-\underset{\underset{O}{\|}}{C}-A-R$$

| Comp. No. | R | A | Physical data |
|---|---|---|---|
| 1.07 | $-CH_2-CH_2-O-C_6H_4-OCH_2-C_6H_4-Cl$ | O | |
| 1.08 | $-CH_2-CH_2-O-C_6H_4-OCH_2-C_6H_4-NO_2$ | O | |
| 1.09 | $-CH_2-CH_2-O-C_6H_4-OCH_2-C_6H_4-CN$ | O | |
| 1.10 | $-CH_2-CH_2-O-C_6H_4-OCH_2-C_6H_4-CH_3$ | O | |
| 1.11 | $-CH_2-CH_2-O-C_6H_4-OCH_2-C_6H_4-CF_3$ | O | |
| 1.12 | $-CH_2-CH_2-O-C_6H_4-OCH_2-C_6H_4-O-CH_3$ | O | |
| 1.13 | $-CH_2-CH_2-O-C_6H_4-OCH_2-C_6H_4(m\text{-}NO_2)$ | O | |
| 1.14 | $-CH_2-CH_2-O-C_6H_4-OCH_2-C_6H_3(2,3\text{-}(CH_3)_2)$ | O | |
| 1.15 | $-CH_2-CH_2-O-C_6H_4-OCH_2-C_6H_4(o\text{-}NO_2)$ | O | |
| 1.16 | $-CH_2-CH_2-O-C_6H_4-OCH_2-\text{(2-Cl-pyridin-5-yl)}$ | O | |
| 1.17 | $-CH_2-CH_2-O-C_6H_4-OCH_2-\text{(3,4-methylenedioxyphenyl)}$ | O | |
| 1.18 | $-CH_2-CH_2-O-C_6H_4-OCH_2-\text{(pyridin-2-yl)}$ | NH | |

TABLE 1-continued $$F_2C=CH-CH_2-\underset{\underset{O}{\|}}{C}-A-R$$

| Comp. No. | R | A | Physical data |
|---|---|---|---|
| 1.19 | —CH₂—CH₂—O—⟨C₆H₄⟩—OCH₂—(thiadiazole)—CH₂OC₂H₅ | NH | |
| 1.20 | —CH₂—CH₂—O—⟨C₆H₄⟩—O—CH₂—N(triazole) | NH | |
| 1.21 | —CH₂—CH₂—O—⟨C₆H₄⟩—O—C(=O)—⟨C₆H₅⟩ | O | |
| 1.22 | —CH₂—CH₂—O—⟨C₆H₄⟩—O—C(=O)—O—⟨C₆H₅⟩ | O | |
| 1.23 | —CH₂—CH₂—O—⟨C₆H₄⟩—O—C(=O)—HN—⟨C₆H₅⟩ | O | |
| 1.24 | —CH₂—CH₂—O—⟨C₆H₄⟩—O—C(=S)—HN—⟨C₆H₅⟩ | O | |

TABLE 2

$$F_2C=CH-(CH_2)_3-\underset{\underset{O}{\|}}{C}-A-R$$

| Comp. No. | R | A | Physical data |
|---|---|---|---|
| 2.01 | —CH₂—CH₂—O—⟨C₆H₄⟩—O—⟨C₆H₅⟩ | O | $n_D^{23}$:1.5246 |
| 2.02 | —CH₂—CH₂—O—⟨C₆H₄⟩—S—⟨C₆H₅⟩ | O | $n_D^{23}$:1.5538 |
| 2.03 | —CH₂—CH₂—O—⟨C₆H₄⟩—O—(2-pyridyl) | O | $n_D^{23}$:1.5250 |
| 2.04 | —CH₂—CH₂—O—⟨C₆H₄⟩—O—C(=N—N=C(CH₃))—S— | O | $n_D^{23}$:1.5212 |
| 2.05 | —CH₂—CH₂—O—⟨C₆H₄⟩—OCH₂—⟨C₆H₅⟩ | O | $n_D^{23}$:1.5238 |
| 2.06 | —CH₂—CH(CH₃)—O—⟨C₆H₄⟩—O—⟨C₆H₅⟩ | O | $n_D^{23}$:1.5180 |

TABLE 2-continued $$F_2C=CH-(CH_2)_3-\underset{\underset{O}{\|}}{C}-A-R$$

| Comp. No. | R | A | Physical data |
|---|---|---|---|
| 2.07 | −CH$_2$−CH$_2$−O−(C$_6$H$_4$)−OCH$_2$−(C$_6$H$_4$)−F | O | m.p.:50–52° C. |
| 2.08 | −CH$_2$−CH$_2$−O−(C$_6$H$_4$)−OCH$_2$−(C$_6$H$_4$)−Cl | O | m.p.:37–38° C. |
| 2.09 | −CH$_2$−CH$_2$−O−(C$_6$H$_4$)−OCH$_2$−(C$_6$H$_4$)−NO$_2$ | O | m.p.:54–55° C. |
| 2.10 | −CH$_2$−CH$_2$−O−(C$_6$H$_4$)−OCH$_2$−(C$_6$H$_4$)−CN | O | m.p.:36–37° C. |
| 2.11 | −CH$_2$−CH$_2$−O−(C$_6$H$_4$)−OCH$_2$−(C$_6$H$_4$)−CH$_3$ | O | m.p.:53–54° C. |
| 2.12 | −CH$_2$−CH$_2$−O−(C$_6$H$_4$)−OCH$_2$−(C$_6$H$_4$)−CF$_3$ | O | m.p.:45–46° C. |
| 2.13 | −CH(CH$_3$)−CH(CH$_3$)−O−(C$_6$H$_4$)−O−(C$_6$H$_5$) | O | $n_D^{23}$:1.5092 |
| 2.14 | −CH$_2$−CH$_2$−O−(C$_6$H$_4$)−OCH$_2$−(C$_6$H$_4$)−O−CH$_3$ | O | m.p.:89–90° C. |
| 2.15 | −CH$_2$−CH$_2$−O−(C$_6$H$_4$)−OCH$_2$−(C$_6$H$_4$)(3-NO$_2$) | O | $n_D^{27}$:1.5362 |
| 2.16 | −CH$_2$−CH$_2$−O−(C$_6$H$_4$)−OCH$_2$−(C$_6$H$_3$)(3-CH$_3$)(4-CH$_3$) | O | m.p.:42–43° C. |
| 2.17 | −CH$_2$−CH$_2$−O−(C$_6$H$_4$)−OCH$_2$−(C$_6$H$_4$)(2-NO$_2$) | O | |
| 2.18 | −CH$_2$−CH$_2$−O−(C$_6$H$_4$)−OCH$_2$−(pyridyl)−Cl | O | |

TABLE 2-continued $$F_2C=CH-(CH_2)_3-\underset{\underset{O}{\|}}{C}-A-R$$

| Comp. No. | R | A | Physical data |
|---|---|---|---|
| 2.19 | —CH$_2$—CH$_2$—O—⟨C$_6$H$_4$⟩—OCH$_2$—⟨C$_6$H$_3$(OCH$_2$O)⟩ | O | |
| 2.20 | —CH$_2$—CH$_2$—O—⟨C$_6$H$_4$⟩—O—⟨C$_6$H$_5$⟩ | NH | m.p.:64–65° C. |
| 2.21 | —CH$_2$—CH$_2$—O—⟨C$_6$H$_4$⟩—OCH$_2$—⟨pyridyl⟩ | NH | |
| 2.22 | —CH$_2$—CH$_2$—O—⟨C$_6$H$_4$⟩—O—C(=O)—⟨C$_6$H$_5$⟩ | O | m.p.:50–51° C. |
| 2.23 | —CH$_2$—CH$_2$—O—⟨C$_6$H$_4$⟩—O—C(=O)—O—⟨C$_6$H$_5$⟩ | O | $n_D^{23}$:1.5144 |
| 2.24 | —CH$_2$—CH$_2$—O—⟨C$_6$H$_4$⟩—O—C(=O)—HN—⟨C$_6$H$_5$⟩ | O | |
| 2.25 | —CH$_2$—CH$_2$—O—⟨C$_6$H$_4$⟩—O—C(=S)—HN—⟨C$_6$H$_5$⟩ | O | |
| 2.26 | —CH$_2$—CH$_2$—O—⟨C$_6$H$_4$⟩—OCH$_2$—⟨C$_6$H$_4$⟩—C(CH$_3$)$_3$ | O | m.p.:35–36° C. |
| 2.27 | —CH$_2$—CH$_2$—O—⟨C$_6$H$_4$(OCH$_2$—⟨C$_6$H$_4$-NO$_2$⟩)⟩ | O | $n_D^{23}$:1.5367 |

TABLE 3

$$F_2C=CH-(CH_2)_5-\underset{\underset{O}{\|}}{C}-A-R$$

| Comp. No. | R | A | Physical data |
|---|---|---|---|
| 3.01 | —CH$_2$—CH$_2$—O—⟨C$_6$H$_4$⟩—O—⟨C$_6$H$_5$⟩ | O | $n_D^{20}$:1.5200 |
| 3.02 | —CH$_2$—CH$_2$—O—⟨C$_6$H$_4$⟩—OCH$_2$—⟨C$_6$H$_5$⟩ | O | |

TABLE 3-continued $$F_2C=CH-(CH_2)_5-\underset{\underset{O}{\|}}{C}-A-R$$

| Comp. No. | R | A | Physical data |
|---|---|---|---|
| 3.03 | −CH₂−CH₂−O−(C₆H₄)−OCH₂−(2-pyridyl) | O | |
| 3.04 | −CH₂−CH₂−O−(C₆H₄)−O−C(=S)−N=N−C(CH₂−O−C₂H₅)= | O | |
| 3.05 | −CH₂−CH₂−O−(C₆H₄)−O−C(=S)−CH=CH−(5-Br-thienyl) | O | |
| 3.06 | −CH₂−CH₂−O−(C₆H₄)−OCH₂−(C₆H₄)−F | O | |
| 3.07 | −CH₂−CH₂−O−(C₆H₄)−OCH₂−(C₆H₄)−Cl | O | |
| 3.08 | −CH₂−CH₂−O−(C₆H₄)−OCH₂−(C₆H₄)−NO₂ | O | |
| 3.09 | −CH₂−CH₂−O−(C₆H₄)−OCH₂−(C₆H₄)−CN | O | |
| 3.10 | −CH₂−CH₂−O−(C₆H₄)−OCH₂−(C₆H₄)−CH₃ | O | |
| 3.11 | −CH₂−CH₂−O−(C₆H₄)−OCH₂−(C₆H₄)−CF₃ | O | |
| 3.12 | −CH₂−CH₂−O−(C₆H₄)−OCH₂−(C₆H₄)−O−CH₃ | O | |
| 3.13 | −CH₂−CH₂−O−(C₆H₄)−OCH₂−(3-NO₂-C₆H₄) | O | |
| 3.14 | −CH₂−CH₂−O−(C₆H₄)−OCH₂−(3,4-(CH₃)₂-C₆H₃) | O | |

TABLE 3-continued $$F_2C=CH-(CH_2)_5-\underset{\underset{O}{\|}}{C}-A-R$$

| Comp. No. | R | A | Physical data |
|---|---|---|---|
| 3.15 | —CH₂—CH₂—O—(C₆H₄)—OCH₂—(C₆H₄)—NO₂ (ortho) | O | |
| 3.16 | —CH₂—CH₂—O—(C₆H₄)—OCH₂—(2-chloropyridin-5-yl) | O | |
| 3.17 | —CH₂—CH₂—O—(C₆H₄)—OCH₂—(3,4-methylenedioxyphenyl) | O | |
| 3.18 | —CH₂—CH₂—O—(C₆H₄)—OCH₂—(pyridin-2-yl) | NH | |
| 3.19 | —CH₂—CH₂—O—(C₆H₄)—OCH₂—(5-ethoxymethyl-1,3,4-thiadiazol-2-yl) | NH | |
| 3.20 | —CH₂—CH₂—O—(C₆H₄)—O—CH₂—N(1,2,4-triazol-1-yl) | NH | |

TABLE 4

$$F_2C=CH-(CH_2)_7-\underset{\underset{O}{\|}}{C}-A-R$$

| Comp. No. | R | A | Physical data |
|---|---|---|---|
| 4.01 | —CH₂—CH₂—O—(C₆H₄)—O—(C₆H₅) | O | $n_D^{24}$: 1.5139 |
| 4.02 | —CH₂—CH₂—O—(C₆H₄)—S—(C₆H₅) | O | $n_D^{24}$: 1.5391 |
| 4.03 | —CH₂—CH₂—O—(C₆H₄)—O—(pyridin-2-yl) | O | $n_D^{22}$: 1.5143 |
| 4.04 | —CH₂—CH₂—O—(C₆H₄)—O—(4-methyl-1,3-thiazol-2-yl) | O | $n_D^{22}$: 1.5106 |
| 4.05 | —CH₂—CH₂—O—(C₆H₄)—OCH₂—(C₆H₅) | O | m.p.: 44–45° C. |

TABLE 4-continued $F_2C{=}CH{-}(CH_2)_7{-}\underset{\underset{O}{\|}}{C}{-}A{-}R$

| Comp. No. | R | A | Physical data |
|---|---|---|---|
| 4.06 | —CH$_2$—CH(CH$_3$)—O—⟨C$_6$H$_4$⟩—O—⟨C$_6$H$_5$⟩ | O | n$_D^{24}$: 1.5080 |
| 4.07 | —CH$_2$—CH$_2$—O—⟨C$_6$H$_4$⟩—O—⟨C$_6$H$_4$⟩—F | O | |
| 4.08 | —CH$_2$—CH$_2$—O—⟨C$_6$H$_4$⟩—OCH$_2$—⟨C$_6$H$_4$⟩—Cl | O | |
| 4.09 | —CH$_2$—CH$_2$—O—⟨C$_6$H$_4$⟩—OCH$_2$—⟨C$_6$H$_4$⟩—NO$_2$ | O | |
| 4.10 | —CH$_2$—CH$_2$—O—⟨C$_6$H$_4$⟩—OCH$_2$—⟨C$_6$H$_4$⟩—CN | O | |
| 4.11 | —CH$_2$—CH$_2$—O—⟨C$_6$H$_4$⟩—OCH$_2$—⟨C$_6$H$_4$⟩—CH$_3$ | O | |
| 4.12 | —CH$_2$—CH$_2$—O—⟨C$_6$H$_4$⟩—OCH$_2$—⟨C$_6$H$_4$⟩—CF$_3$ | O | |
| 4.13 | —CH(CH$_3$)—CH(CH$_3$)—O—⟨C$_6$H$_4$⟩—O—⟨C$_6$H$_5$⟩ | O | |
| 4.14 | —CH$_2$—CH$_2$—O—⟨C$_6$H$_4$⟩—OCH$_2$—⟨C$_6$H$_4$⟩—O—CH$_3$ | O | |
| 4.15 | —CH$_2$—CH$_2$—O—⟨C$_6$H$_4$⟩—OCH$_2$—⟨C$_6$H$_4$⟩(3-NO$_2$) | O | |
| 4.16 | —CH$_2$—CH$_2$—O—⟨C$_6$H$_4$⟩—OCH$_2$—⟨C$_6$H$_3$⟩(3,4-(CH$_3$)$_2$) | O | |
| 4.17 | —CH$_2$—CH$_2$—O—⟨C$_6$H$_4$⟩—OCH$_2$—⟨C$_6$H$_4$⟩(2-NO$_2$) | O | |
| 4.18 | —CH$_2$—CH$_2$—O—⟨C$_6$H$_4$⟩—OCH$_2$—⟨pyridyl⟩—Cl | O | |

TABLE 4-continued $$F_2C=CH-(CH_2)_7-\underset{\underset{O}{\|}}{C}-A-R$$

| Comp. No. | R | A | Physical data |
|---|---|---|---|
| 4.19 | —CH₂—CH₂—O—C₆H₄—OCH₂—C₆H₃(—O—CH₂—CH₂—O—) | O | |
| 4.20 | —CH₂—CH₂—O—C₆H₄—O—C₆H₅ | NH | m.p.: 73–75° C. |
| 4.21 | —CH₂—CH₂—O—C₆H₄—OCH₂—(2-pyridyl) | NH | |

TABLE 5

$$F_2C=CH-(CH_2)_9-\underset{\underset{O}{\|}}{C}-A-R$$

| Comp. No. | R | A | Physical data |
|---|---|---|---|
| 5.01 | —CH₂—CH₂—O—C₆H₄—O—C₆H₅ | O | m.p.: 30–32° C. |
| 5.02 | —CH₂—CH₂—O—C₆H₄—S—C₆H₅ | O | $n_D^{24}$: 1.5339 |
| 5.03 | —CH₂—CH₂—O—C₆H₄—O—(2-pyridyl) | O | $n_D^{24}$: 1.5246 |
| 5.04 | —CH₂—CH₂—O—C₆H₄—O—C(=N-S-N=)CH₃ | O | $n_D^{22}$: 1.5080 |
| 5.05 | —CH₂—CH₂—O—C₆H₄—OCH₂—C₆H₅ | O | m.p.: 54–65° C. |
| 5.06 | —CH₂—CH(CH₃)—O—C₆H₄—O—C₆H₅ | O | $n_D^{21}$: 1.5056 |
| 5.07 | —CH₂—CH₂—O—C₆H₄—OCH₂—C₆H₄—F | O | m.p.: 50–52° C. |
| 5.08 | —CH₂—CH₂—O—C₆H₄—OCH₂—C₆H₄—Cl | O | m.p.: 54–55° C. |

TABLE 5-continued $$F_2C=CH-(CH_2)_9-\underset{\underset{O}{\|}}{C}-A-R$$

| Comp. No. | R | A | Physical data |
|---|---|---|---|
| 5.09 | $-CH_2-CH_2-O-\text{C}_6\text{H}_4-OCH_2-\text{C}_6\text{H}_4-NO_2$ | O | |
| 5.10 | $-CH_2-CH_2-O-\text{C}_6\text{H}_4-OCH_2-\text{C}_6\text{H}_4-CN$ | O | m.p.: 50–52° C. |
| 5.11 | $-CH_2-CH_2-O-\text{C}_6\text{H}_4-OCH_2-\text{C}_6\text{H}_4-CH_3$ | O | m.p.: 69–71° C. |
| 5.12 | $-CH_2-CH_2-O-\text{C}_6\text{H}_4-OCH_2-\text{C}_6\text{H}_4-CF_3$ | O | m.p.: 45–48° C. |
| 5.13 | $-CH(CH_3)-CH(CH_3)-O-\text{C}_6\text{H}_4-O-\text{C}_6\text{H}_5$ | O | |
| 5.14 | $-CH_2-CH_2-O-\text{C}_6\text{H}_4-OCH_2-\text{C}_6\text{H}_4-O-CH_3$ | O | |
| 5.15 | $-CH_2-CH_2-O-\text{C}_6\text{H}_4-OCH_2-\text{C}_6\text{H}_4(m\text{-}NO_2)$ | O | $n_D^{23}$: 1.5204 |
| 5.16 | $-CH_2-CH_2-O-\text{C}_6\text{H}_4-OCH_2-\text{C}_6\text{H}_3(2,3\text{-}(CH_3)_2)$ | O | m.p.: 46–48° C. |
| 5.17 | $-CH_2-CH_2-O-\text{C}_6\text{H}_4-OCH_2-\text{C}_6\text{H}_4(o\text{-}NO_2)$ | O | |
| 5.18 | $-CH_2-CH_2-O-\text{C}_6\text{H}_4-OCH_2-\text{pyridyl-Cl}$ | O | |
| 5.19 | $-CH_2-CH_2-O-\text{C}_6\text{H}_4-OCH_2-\text{(methylenedioxyphenyl)}$ | O | |
| 5.20 | $-CH_2-CH_2-O-\text{C}_6\text{H}_4-OCH_2-\text{C}_6\text{H}_4(m\text{-}Cl)$ | O | $n_D^{24}$: 1.5161 |

TABLE 5-continued

F$_2$C=CH—(CH$_2$)$_9$—C(=O)—A—R

| Comp. No. | R | A | Physical data |
|---|---|---|---|
| 5.21 | —CH$_2$—CH$_2$—O—C$_6$H$_4$—OCH$_2$—(2-pyridyl-5-CF$_3$) | NH | n$_D^{24}$: 1.4876 |
| 5.22 | —CH$_2$—CH$_2$—O—C$_6$H$_4$—OCH$_2$—(3-Cl-5-CF$_3$-2-pyridyl) | O | n$_D^{24}$: 1.4949 |
| 5.23 | —CH$_2$—CH$_2$—O—C$_6$H$_4$—OCH$_2$—(2-F-C$_6$H$_4$) | O | n$_D^{24}$: 1.5033 |
| 5.24 | —CH$_2$—CH$_2$—O—C$_6$H$_4$—OCH$_2$—(3-F-C$_6$H$_4$) | O | n$_D^{24}$: 1.5035 |
| 5.25 | —CH$_2$—CH(CH$_3$)—O—C$_6$H$_4$—S—C$_6$H$_5$ | O | n$_D^{24}$: 1.5291 |
| 5.26 | —CH$_2$—CH$_2$—O—C$_6$H$_4$—O—C$_6$H$_5$ | NH | m.p.: 86–88° C. |
| 5.27 | —CH$_2$—CH$_2$—O—C$_6$H$_4$—OCH$_2$—(2-pyridyl) | NH | |
| 5.28 | —CH$_2$—CH$_2$—O—C$_6$H$_4$—O—C(=O)—C$_6$H$_5$ | O | m.p.: 45–46° C. |
| 5.29 | —CH$_2$—CH$_2$—O—C$_6$H$_4$—O—C(=O)—O—C$_6$H$_5$ | O | n$_D^{23}$: 1.5031 |
| 5.30 | —CH$_2$—CH$_2$—O—C$_6$H$_4$—O—C(=O)—NH—C$_6$H$_5$ | O | |
| 5.31 | —CH$_2$—CH$_2$—O—C$_6$H$_4$—O—C(=S)—NH—C$_6$H$_5$ | O | |
| 5.32 | —CH$_2$—CH$_2$—O—C$_6$H$_4$—OCH$_2$—(4-tBu-C$_6$H$_4$) | O | n$_D^{23}$: 1.5082 |

TABLE 6

$$Q-\underset{\underset{O}{\|}}{C}-O-CH_2-CH_2-O-C_6H_4-O-C_6H_5$$

| Comp. No. | Q | Physical data |
|---|---|---|
| 6.01 | $F_2C=C(CH_3)-CH_2-$ | |
| 6.02 | $F_2C=C(CH_3)-(CH_2)_3-$ | |
| 6.03 | $F_2C=C(CH_3)-(CH_2)_5-$ | |
| 6.04 | $F_2C=C(CH_3)-(CH_2)_7-$ | |
| 6.05 | $F_2C=C(CH_3)-(CH_2)_9-$ | |
| 6.06 | $FClC=C(CH_3)-(CH_2)_3-$ | |
| 6.07 | $F_2C=C(CH_3)-(CH_2)_3-$ | |
| 6.08 | $FClC=C(CH_3)-(CH_2)_3-$ | |
| 6.09 | $FClC=C(CH_3)-(CH_2)_9-$ | $n_D^{21}$: 1.5232 |

FORMULATION EXAMPLES (% = per cent by weight)

| Example F1: Emulsion concentrates | a) | b) | c) |
|---|---|---|---|
| Active ingredient No. 1.01 | 25% | 40% | 50% |
| Calcium dodecylbenzenesulfonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient No. 1.01 | 80% | 10% | 5% | 95% |
| Ethylene glycol monomethyl ether | 20% | — | — | — |
| Polyethylene glycol MW 400 | — | 70% | — | — |
| N-Methyl-2-pyrrolidone | — | 20% | — | — |
| Epoxidised coconut oil | — | — | 1% | 5% |
| Petroleum spirit (boiling range 160–190° C.) | — | — | 94% | — |

The solutions are suitable for use in the form of microdrops.

| Example F3: Granules | a) | b) | c) | d) |
|---|---|---|---|---|
| Active ingredient No. 1.01 | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in methylene chloride, the solution is sprayed onto the carrier, and the solvent is subsequently evaporated in vacuo.

| Example F4: Dusts | a) | b) |
|---|---|---|
| Active ingredient No. 1.01 | 2% | 5% |
| Highly disperse silica | 1% | 5% |
| Talc | 97% | — |
| Kaolin | — | 90% |

A ready-to-use dust is obtained by intimately mixing the carriers with the active ingredient.

| Example F5: Wettable powders | a) | b) | c) |
|---|---|---|---|
| Active ingredients No. 5.01 | 25% | 50% | 75% |
| Sodium ligninsulfonate | 5% | 5% | — |
| Sodium lauryl sulfate | 3% | — | 5% |
| Sodium diisobutylnaphthalene-sulfonate | — | 6% | 10% |
| Octylphenol polyethylene glycol ether (7–8 mol of EO) | — | 2% | — |
| Highly disperse silica | 5% | 10% | 10% |
| Kaolin | 62% | 27% | — |

The active ingredient is mixed with the additives and ground thoroughly in a suitable mill. This gives wettable powders which can be diluted with water to give suspensions of any desired concentration.

| Example F6: Emulsion concentrate | |
|---|---|
| Active ingredient No. 5.01 | 10% |
| Octylphenol polyethylene glycol ether (4–5 mol of EO) | 3% |
| Calcium dodecylbenzenesulfonate | 3% |
| Castor oil polyglycol ether (36 mol of EO) | 4% |
| Cyclohexanone | 30% |

-continued

| Example F6: Emulsion concentrate | |
|---|---|
| Xylene mixture | 50% |

Emulsions of any desired concentration can be prepared from this concentrate by dilution with water.

| Example F7: Dusts | a) | b) |
|---|---|---|
| Active ingredient No. 5.01 | 5% | 8% |
| Talc | 95% | — |
| Kaolin | — | 92% |

Ready-to-use dusts are obtained by mixing the active ingredient with the carrier and grinding the mixture on a suitable mill.

| Example F8: Extruder granules | |
|---|---|
| Active ingredient No. 5.01 | 10% |
| Sodium ligninsulfonate | 2% |
| Carboxymethylcellulose | 1% |
| Kaolin | 87% |

The active ingredient is mixed with the additives, and the mixture is ground and moistened with water. This mixture is extruded, granulated and subsequently dried in a stream of air.

| Example F9: Coated granules | |
|---|---|
| Active ingredient No. 5.01 | 3% |
| Polyethylene glycol (MW 200) | 3% |
| Kaolin | 94% |

In a mixer, the finely ground active ingredient is applied uniformly to the kaolin which has been moistened with polyethylene glycol. Dust-free coated granules are obtained in this manner.

| Example F10: Suspension concentrate | |
|---|---|
| Active ingredient No. 5.01 | 40% |
| Ethylene glycol | 10% |
| Nonylphenol polyethylene glycol ether (15 mol of EO) | 6% |
| Sodium ligninsulfonate | 10% |
| Carboxymethylcellulose | 1% |
| Silicone oil in the form of a 75% aqueous emulsion | 1% |
| Water | 32% |

The finely ground active ingredient is mixed intimately with the additives. This gives a suspension concentrate from which suspensions of any desired concentration can be prepared by dilution with water.

BIOLOGICAL EXAMPLES

Example B1: Activity against Boophilus microplus

Adult female ticks which have sucked themselves full are attached to a PVC board and covered with a cottonwool ball. The test animals are treated by pouring 10 ml of an aqueous test solution comprising 125 ppm of the active ingredient to be tested over them. The cottonwool ball is subsequently removed, and the ticks are incubated for 4 weeks for oviposition. The activity against Boophilus microplus is demonstrated either, in the case of the female, as mortality or sterility, or, in the case of the eggs, as ovicidal activity. In this test, the compounds of Tables 1 to 6 exhibit a good activity. An activity of over 80% is shown, in particular, by compound Nos. 1.01, 2.01 to 2.06, 2.10, 2.12, 2.14 to 2.16, 2.20, 2.22, 2.23, 2.26, 3.01, 4.01, 4.02, 4.05, 4.06, 4.20, 5.01 to 5.03, 5.05, 5.06 and 5.20 to 5.25.

Example B2: Activity against Nilaparvata lugens

Rice plants are treated with a spray mixture prepared with an aqueous emulsion and comprising 400 ppm of the active ingredient. After the spray coating has dried on, the rice plants are populated with plant hopper larvae in stages 2 and 3. The test is evaluated after 21 days. The percentage reduction in population (% activity) is determined by comparing the number of surviving plant hoppers on the treated plants with the number of plant hoppers on the untreated plants. In this test, the compounds of Tables 1 to 6 exhibit a good activity. An activity of over 80% is shown, in particular, by compound Nos. 1.01, 2.01 to 2.03, 2.07, 2.08, 2.10 to 2.16, 2.20, 2.22, 2.23, 2.26, 3.01, 4.01 to 4.06, 4.20, 5.01 to 5.06, 5.08, 5.10 to 5.12, 5.15, 5.16 and 5.20 to 5.25.

Example B3: Activity against Ctenocephalides felis 20 to 25 flea eggs are placed into a horizontally positioned 50 ml tissue culture flask into which 15 g of flea larvae nutrient medium comprising 100 ppm of the active ingredient to be tested have previously been introduced. The test flasks are incubated in an incubator at 26° to 27° C. and an atmospheric humidity of 60–70%. After 21 days, the flasks are checked for the presence of adult fleas, unhatched pupae and larvae.

In this test, the compounds of Tables 1 to 6 shown a good activity against Ctenocephalides fells. An activity of over 80% is shown, in particular, by compound Nos. 1.01, 2.02 to 2.08, 2.10 to 2.15, 2.22, 2.23, 2.26, 3.01, 4.03, 4.04, 5.08 and 5.10 to 5.12.

Example B4: Activity against Aphis craccivora

Pea seedlings are infected with Aphis craccivora, subsequently sprayed with a spray mixture comprising 400 ppm of the active ingredient, and incubated at 20° C. The test is evaluated after 3 and 6 days. The percentage reduction in population (% activity) is determined by comparing the number of dead aphids on the treated plants with those on the untreated plants.

In this test, the compounds of Tables 1 to 6 exhibit a good activity. An activity of over 80% is shown, in particular, by compound Nos. 1.01, 2.01 to 2.07, 2.10 to 2.13, 2.22, 2.23, 3.01, 5.05 and 5.20 to 5.25.

Example B5: Systemic activity against Nilaparvata lugens

Pots containing rice plants are placed into an aqueous emulsion solution comprising 400 ppm of the active ingredient. The rice plants are subsequently populated with larvae in stages 2 and 3. The test is evaluated 6 days later. The percentage reduction in population (% activity) is determined by comparing the numbers of plant hoppers on the treated plants with those on the untreated plants.

In this test, the compounds of Tables 1 to 6 exhibit a good activity. An activity of over 80% is shown, in particular, by compound Nos. 1.01, 2.01 to 2.08, 2.10 to 2.16, 2.20, 2.22, 2.23, 2.26, 3.01, 4.01 to 4.06, 4.20, 5.01 to 5.08, 5.10 to 5.12, 5.15, 5.16 and 5.20 to 5.25.

Example B6: Activity against Panonychus ulmi (OP- and carb.- resistant)

Apple seedlings are populated with adult females of Panonychus ulmi. After seven days, the infested plants are sprayed to drip point with an aqueous emulsion comprising 400 ppm of the test compound and grown in the greenhouse. The test is evaluated after 14 days. The percentage reduction in population (% activity) is determined by comparing the number of dead spider mites on the treated plants with those on the untreated plants. In this test, the compounds of Tables 1 to 6 exhibit a good activity. An activity of over 80% is shown, in particular, by compound Nos. 1.01, 2.01, 2.07, 2.08, 2.10, 2.12 to 2.16, 2.22, 2.23, 2.26, 3.01, 4.01, 4.02, 4.06, 5.01 to 5.03, 5.05, 5.06, 5.08, 5.10, 5.11, 5.15, 5.16 and 5.20 to 5.25.

Example B7: Activity against Nephotettix cincticeps

Rice plants are treated with a spray mixture prepared with an aqueous emulsion and comprising 400 ppm of the active ingredient. After the spray coating has dried on, the rice plants are populated with leaf hopper larvae in stages 2 and 3. The test is evaluated 21 days later. The percentage reduction in population (% activity) is determined by comparing the number of surviving leaf hoppers on the treated plants with those on the untreated plants.

In this test, the compounds of Tables 1 to 6 exhibit a good activity. An activity of over 80% is shown, in particular, by compound Nos. 1.01, 2.01, 2.02, 2.03, 2.06, 2.07, 2.10 to 2.12, 2.14 to 2.16, 2.23, 2.26, 3.01, 4.01, 4.02, 4.05, 4.06, 5.01 to 5.03, 5.05, 5.10 to 5.12, 5.15, 5.16, 5.20, 5.22, 5.24 and 5.25.

Example B8: Activity against Bemisia tabaci

Dwarf bean plants are placed into gauze cages and populated with adult Bemisia tabaci specimens (white fly). After oviposition has taken place, all adults are removed and, 10 days later, the plants with the nymphs located thereon are treated with a spray mixture of the active ingredients to be tested (concentration 400 ppm), which has been prepared with an aqueous emulsion. The test is evaluated for hatching percentages 14 days after the active ingredient has been applied by comparison with the untreated control batches. In this test, the compounds of Tables 1 to 6 exhibit a good activity. An activity of over 80% is shown, in particular, by compound Nos. 1.01, 2.01 to 2.08, 2.10 to 2.16, 2.22, 2.23, 3.01, 4.01, 4.02, 4.05, 4.06, 5.02, 5.03, 5.06 to 5.08, 5.10, 5.11, 5.20, 5.21 and 6.09.

Example B9: Activity against Tetranychus urticae

Young bean plants are populated with a mixed population of Tetranychus urticae and, after 1 day, sprayed with a spray mixture prepared with an aqueous emulsion and comprising 400 ppm of the active ingredient. The plants are subsequently incubated for 6 days at 25° C and then evaluated. The percentage reduction in population (% activity) is determined by comparing the number of dead eggs, larvae and adults on the treated plants with those on the untreated ones.

In this test, the compounds of Tables 1 to 6 exhibit a good activity. An activity of over 80% is shown, in particular, by compound Nos. 1.01, 2.01 to 2.08, 2.10, 2.12 to 2.16, 2.22, 2.23, 2.26, 3.01, 4.01 to 4.06, 4.20, 5.01 to 5.06, 5.08, 5.10 to 5.12, 5.15, 5.16 and 5.20 to 5.25.

Example B10: Activity against Heliothis virescens caterpillars

Young soybean plants are sprayed with a spray mixture prepared with an aqueous emulsion and comprising 400 ppm of the active ingredient. After the spray coating has dried on, the soybean plants are populated with 10 Heliothis virescens in the first larval stage and placed into a plastic container. The test is evaluated after 6 days. The percentage reduction in population, or the percentage reduction in feeding damage (% activity), is determined by comparing the number of dead caterpillars and the feeding damage on the treated plants with those on the untreated plants.

In this test, the compounds of Tables 1 to 6 exhibit a good activity. An activity of over 80% is shown, in particular, by compound Nos. 1.01, 2.01 to 2.08, 2.10 to 2.16, 2.22, 2.23, 2.26, 3.01, 4.01, 4.02, 4.05, 4.06, 4.20, 5.01 to 5.03, 5.05 to 5.08, 5.10 to 5.12, 5.15, 5.16, 5.20 to 5.22, 5.24 and 5.25.

Example B11: Activity against Crocidolomia binotalis caterpillars

Young cabbage plants are sprayed with a spray mixture prepared with an aqueous emulsion and comprising 400 ppm of the active ingredient. After the spray coating has dried on, the cabbage plants are infested with 10 Crocidolomia binotalis in the third larval stage and placed into a plastic container. The test is evaluated after 3 days. The percentage reduction in population, or the percentage reduction in feeding damage (% activity), is determined by comparing the number of dead caterpillars and the feeding damage on the treated plants with those on the untreated plants.

In this test, the compounds of Tables 1 to 6 exhibit a good activity. An activity of over 80% is shown, in particular, by compound Nos. 1.01, 3.01, 5.01, 5.02, 5.05 and 5.20 to 5.25.

Example B12: Activity against adult Anthonomus grandis

Young cotton plants are sprayed with a spray mixture prepared with an aqueous emulsion and comprising 400 ppm of the active ingredient. After the spray coating has dried on, the cotton plants are populated with 10 adult Anthonomus grandis and placed into a plastic container. The test is evaluated after 3 days. The percentage reduction in population, or the percentage reduction in feeding damage (% activity), is determined by comparing the number of dead beetles and the feeding damage on the treated plants with those on the untreated plants.

In this test, the compounds of Tables 1 to 6 exhibit a good activity. An activity of over 80% is shown, in particular, by compound Nos. 1.01, 2.07, 2.08, 2.10 to 2.16, 3.01, 5.01, 5.02, 5.05, 5.10, 5.16 and 5.20 to 5.25.

Example B13: Systemic activity against Myzus persicae

Pea seedlings are infected with Myzus persicae, the roots of the plants are then placed into a spray mixture comprising 400 ppm of the active ingredient, and the plants are incubated at 20° C. The test is evaluated after 3 and 6 days. The percentage reduction in population (% activity) is determined by comparing the number of dead aphids on the treated plants with those on the untreated plants.

In this test, the compounds of Tables 1 to 6 exhibit a good activity. An activity of over 80% is shown, in particular, by compound No. 1.01.

Example B14: Systemic activity against Nephotettix cincticeps

Pots containing rice plants are placed into an aqueous emulsion solution comprising 400 ppm of the active ingredient. The rice plants are subsequently populated with larvae in stages 2 and 3. The test is evaluated after 6 days. The percentage reduction in population (% activity) is determined by comparing the number of leaf hoppers on the treated plants with those on the untreated plants.

In this test, the compounds of Tables 1 to 6 exhibit a good activity. An activity of over 80% is shown, in particular, by compound Nos. 1.01, 2.01 to 2.06, 3.01, 4.01, 4.02, 4.06, 5.01 to 5.03 and 5.24.

Example B15: Ovicidal/larvicidal activity on Heliothis virescens

Heliothis eggs which have been deposited on cotton are sprayed with a spray mixture prepared with an aqueous emulsion and comprising 400 ppm of the active ingredient. After 8 days, the hatching percentage of the eggs and the survival rate of the caterpillars are evaluated by comparing them with untreated control batches (% reduction in population).

In this test, the compounds of Tables 1 to 6 exhibit a good activity. An activity of over 80% is shown, in particular, by compound Nos. 1.01, 2.01 to 2.07, 2.10 to 2.12, 2.15, 2.16, 2.22, 2.23, 2.26, 3.01, 4.01 to 4.06, 4.20, 5.01 to 5.08, 5.10 to 5.12, 5.15, 5.16, 5.20 to 5.26 and 6.09.

Example B16: Activity against Dermanyssus gallinae 2 to 3 ml of a solution comprising 10 ppm of active ingredient and approximately 200 mites in different development stages are placed into a glass container which is open at the top. The container is then sealed with a cotton-wool ball, shaken for 10 minutes until the mites are wetted completely, and then briefly turned over so that the remaining test solution can be absorbed by the cottonwool. After 3 days, the mortality of the mites is determined by counting the dead individuals; it is given as a percentage.

The compounds of Tables 1 to 6 exhibit a good activity against Dermanyssus gallinae. An activity of over 80% is shown, in particular, by compound Nos. 1.01, 2.06, 2.13, 4.01, 4.02, 4.04, 4.05, 4.06 and 5.21.

What is claimed is:

1. A compound of the formula

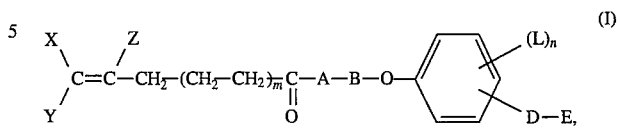

in which

A is oxygen, sulfur or —$NR_1$—;
B is $C_2$-$C_6$alkylene, D-E is —O—E, —S—E, —O—$CH_2$—E, —O—C(=O)—E, —O—C(=O)—O—E, —O—C(=O)—N(H)—E or —O—C(=S)—N(H)—E;
E is phenyl; phenyl which is substituted by one to three substituents selected from the group, consisting of halogen, $C_1$-$C_4$alkyl, halo-$C_1$-$C_4$alkyl, $C_1$-$C_4$alkoxy, halo-$C_1$-$C_4$alkoxy, cyano, nitro and methylenedioxy; a five-membered aromatic heterocycle which has one to three hetero atoms selected from the group, consisting of nitrogen, oxygen and sulfur; a five-membered aromatic heterocycle which has one to three hetero atoms selected from the group, consisting of nitrogen, oxygen and sulfur, and which is substituted by one or two substituents selected from the group, consisting of halogen, $C_1$-$C_4$alkyl and $C_1$-$C_4$haloalkyl; a six-membered aromatic heterocycle which has one to three nitrogen atoms; or a six-membered aromatic heterocycle which has one to three nitrogen atoms and which is substituted by one or two substituents selected from the group, consisting of halogen, $C_1$-$C_4$alkyl and $C_1$-$C_4$haloalkyl;
L is halogen or methyl;
X is fluorine;
Y is chlorine or fluorine;
Z is hydrogen, fluorine or methyl;
m is the number zero, one, two, three, four or five;
n is the number zero, one or two and
$R_1$ is hydrogen, $C_1$-$C_4$alkyl, phenylthio or tolylthio, in free form or, where appropriate, in salt form.

2. A compound as claimed in claim 1 of the formula I in which A is oxygen.

3. A compound as claimed in claim 2 of the formula I in which B is an ethylene bridge.

4. A compound as claimed in claim 1 of the formula I in which A is a bridge —NH—.

5. A compound as claimed in claim 1 of the formula I in which n is zero.

6. A compound as claimed in claim 1 of the formula I in which D is —O—.

7. A compound as claimed in claim 1 of the formula I in which E is phenyl, pyridyl, thiadiazolyl, phenyl which is substituted by one or two substituents selected from the group, consisting of cyano, nitro, halogen, $C_1$-$C_4$alkyl and $C_1$-$C_4$haloalkyl, pyridyl which is substituted by one or two substituents selected from the group, consisting of halogen, $C_1$-$C_4$alkyl and halo-$C_1$-$C_4$alkyl, or $C_1$-$C_4$alkylthiazolyl.

8. A compound as claimed in claim 1 of the formula I in which m is zero, one or four.

9. A compound as claimed in claim 1 of the formula I in which Y is fluorine and Z is hydrogen.

10. A compound as claimed in claim 1 of the formula I in which D is —O—$CH_2$—.

11. A compound as claimed in claim 1 of the formula I in which D is —O—CO— or —O—CO—O—.

12. A compound as claimed in claim 2 of the formula I in which n is zero.

13. A compound as claimed in claim 12 of the formula I in which D is oxygen or sulfur.

14. A compound as claimed in claim 2 of the formula I in which D is —O—CH$_2$—.

15. A compound as claimed in claim 6 of the formula I in which E is a substituted or unsubstituted phenyl, thiadiazolyl or pyridyl group.

16. A compound as claimed in claim 3 of the formula I in which n is zero, D is oxygen, sulfur or —O—CH$_2$, E is phenyl, pyridyl, thiadiazolyl, phenyl which is substituted by one or two substituents selected from the group, consisting of cyano, nitro, halogen, C$_1$–C$_4$alkyl and C$_1$–C$_4$haloalkyl, pyridyl which is substituted by one or two substituents selected from the group, consisting of halogen, C$_{1-4}$alkyl and halo-C$_1$–C$_4$alkyl, or C$_1$–C$_4$alkylthiazolyl, m is zero, one or four, Y is fluorine and Z is hydrogen.

17. A compound as claimed in claim 16 of the formula I, in which m is 1, B is —CH$_2$CH$_2$—, D-E is —O—CH$_2$—E and E is 4-trifluoromethylphenyl.

18. A compound as claimed in claim 1 of the formula I selected from the group, consisting of the compounds
2-(4-phenoxyphenoxy)ethyl-4,4-difluorobut-3-enoate,
2-(4-benzyloxyphenoxy)ethyl-4,4-difluorobut-3-enoate,
2-[4-(4-methyl)benzyloxyphenoxy]ethyl-4,4-difluorobut-3-enoate,
2-(4-phenoxyphenoxy)ethyl-6,6-difluorohex-5-enoate,
2-(4-benzyloxyphenoxy)ethyl-6,6-difluorohex-5-enoate,
2-(4-phenoxyphenoxy)ethyl-8,8-difluorooct-7-enoate,
2-(4-benzyloxyphenoxy)ethyl-8,8-difluorooct-7-enoate,
2-(4-phenoxyphenoxy)ethyl-10,10-difluorodec-9-enoate,
2-(4-benzyloxyphenoxy)ethyl-10,10-difluorodec-9-enoate,
2-(4-phenoxyphenoxy)ethyl-12,12-difluorododec-11-enoate and
2-(4-benzyloxyphenoxy)ethyl 12,12-difluorododec-11-enoate.

19. A pesticidal composition, which comprises at least one compound as claimed in claim 1 of the formula I, in free form or, where appropriate, in agrochemically utilisable salt form, as active ingredient and at least one auxiliary.

20. A composition as claimed in claim 19 for controlling insects or arachnids.

21. A method of comrolling pests, which comprises applying, as active ingredient, a compound as claimed in claim 1 of the formula I, in free form or, where appropriate, in agrochemically utilisable salt form, to the pests or their environment.

22. A method as claimed in claim 21 for controlling insects or arachnids.

\* \* \* \* \*